United States Patent [19]

Sakuma et al.

[11] Patent Number: 5,009,898

[45] Date of Patent: Apr. 23, 1991

[54] ANTIMICROBIAL HYDROXYAPATITE POWDERS AND METHODS FOR PREPARING THEM

[75] Inventors: Shuji Sakuma; Kiminori Atsumi; Keijiro Fujita, all of Tokyo, Japan

[73] Assignee: Kabushiki Kaisha Sangi, Tokyo, Japan

[21] Appl. No.: 409,076

[22] Filed: Sep. 19, 1989

[30] Foreign Application Priority Data

Sep. 29, 1988 [JP] Japan .................... 63-242389
Apr. 14, 1989 [JP] Japan ...................... 1-92999
May 18, 1989 [JP] Japan .................... 63-122958

[51] Int. Cl.$^5$ .................. A61K 33/38; A61K 33/30; A61K 33/34

[52] U.S. Cl. .................. 424/618; 106/35; 423/308; 424/57; 424/417; 424/421; 424/422; 424/423; 424/489; 424/491; 424/602; 424/630; 424/641

[58] Field of Search ............... 424/417, 421, 422, 423, 424/489, 491, 630, 641, 57, 602, 618; 106/35; 423/308

[56] References Cited

U.S. PATENT DOCUMENTS

| | | | |
|---|---|---|---|
| 3,873,327 | 3/1975 | Duff | 106/35 |
| 3,913,229 | 10/1975 | Driskell et al. | 106/35 |
| 4,048,300 | 9/1977 | Tomlinson et al. | 424/57 |
| 4,097,935 | 7/1978 | Jarcho | 106/35 |
| 4,108,980 | 8/1978 | Duff | 424/57 |
| 4,139,599 | 2/1979 | Tomlinson et al. | 424/57 |
| 4,149,894 | 4/1979 | Ebihara et al. | 423/308 |
| 4,224,072 | 9/1980 | Stewart | 106/35 |
| 4,308,064 | 12/1981 | Takami et al. | 106/35 |
| 4,327,079 | 4/1982 | Aoki | 424/57 |
| 4,342,741 | 8/1982 | Aoki | 424/57 |
| 4,518,430 | 5/1985 | Brown et al. | 106/35 |
| 4,542,167 | 9/1985 | Aoki | 106/35 |
| 4,612,053 | 9/1986 | Brown et al. | 106/35 |
| 4,634,589 | 1/1987 | Scheller | 424/57 |
| 4,673,355 | 6/1987 | Farris et al. | 106/35 |
| 4,710,372 | 12/1987 | Scheller | 424/57 |
| 4,781,904 | 11/1988 | Tagaya et al. | 423/308 |
| 4,794,171 | 12/1988 | Tagaya et al. | 423/308 |
| 4,812,404 | 3/1989 | Kuboki et al. | 435/176 |
| 4,880,610 | 11/1989 | Constantz | 423/309 |
| 4,885,207 | 12/1989 | Johnson et al. | 435/176 |

*Primary Examiner*—Shep K. Rose
*Attorney, Agent, or Firm*—Finnegan, Henderson, Farabow, Garrett & Dunner

[57] ABSTRACT

Antimicrobial hydroxyapatite powders containing hydroxyapatite powder and metal ions selected from silver, copper and zinc ions or one or more antimicrobial agents selected from hinokitiol, tannin, lysozyme, protamine and sorbic acid.

4 Claims, No Drawings

ANTIMICROBIAL HYDROXYAPATITE POWDERS AND METHODS FOR PREPARING THEM

BACKGROUND OF THE INVENTION

1. Field of the Invention

This invention relates to antimicrobial hydroxyapatite powders, wherein metal ions having an antimicrobial property such as silver, copper and zinc ions, or organic antimicrobial agents such as hinokitiol, tannin, lysozyme, protamine and sorbic acid are included in hydroxyapatite powders having good affinity for a living body. These powders are widely used in the medical, dental and hygienic fields as artificial bone, artificial root of a tooth, dentifrice, dental cement, supplement for bone deficit and cosmetic materials.

2. Description of the Prior Art

Antimicrobial agents are widely used in the fields of drugs, medical instruments, cosmetics, foods, kichenwares, package materials, filters, clothings and miscellaneous goods. They are particularly useful in places where many people eat, drink, breathe or otherwise congregate.

Antimicrobial agents are classified into two groups, that is, the synthetic or natural inorganic group and the synthetic or natural organic group. In practice, the antimicrobial agents now used are the organic substances. Inorganic antimicrobial agents are not yet in use because the antimicrobial properties of the metals and salts thereof depend upon metal ions. As a result, they can be only used in aqueous solutions and have strong toxicity and defects relating to coloring and change of color. However, organic antimicrobial agents also have defects such as high volability, low heat resistance, coloring and high solubility for water and organic solvents. Thus their fields of use are also limited.

Accordingly, various proposals have been made to overcome the defects of organic antimicrobial agents. For example, combinations of hinokitiol with alum and calcium salt have been proposed to prevent the coloring of hinokitiol (Japanese Patent Publication 59-224677) or the salt and inclusion compound thereof are used (Japanese Patent Publication 61-108359).

Generally, materials to be used for a living body are disinfected by heating or treating with ethyleneoxide and are preserved in the disinfected state to prevent the breeding and adhesion of unwanted bacteria. But, the problem of disinfecting with ethyleneoxides is that the ethyleneoxides are retained in said materials and thus contaminate the materials. Also the materials are often used in treating localized bodily infections, and hence the possibility for breeding bacteria in the infections may be high.

If the composition of hydroxyapatite is substantially the same as the composition of living body bone, then it has good affinity for the living body and is superior as a body material. However, proteins, amino acids and other organic substances are easily absorbed in hydroxyapatite, so then bacteria are also easily absorbed in hydroxyapatite. Accordingly, when hydroxyapatite is used as a living body material, it is necessary to consider the contamination of hydroxyapatite with bacteria. To solve the problem of contamination of hydroxyapatite, it has been proposed to use antimicrobial agents with hydroxyapatite. However, because the antimicrobial agents usually used are organic substances having low heat resistance and high solubility, the heat treatment of the agents is difficult. Thus the antimicrobial agents usually used are difficult to use as materials for the living body and medical instruments.

Even if the organic antimicrobial agents have high anticontamination properties, the use of such the agents must be limited because of unfavorable problems such as change in taste, smell and discoloration that may occur when added directly to foods.

When said agents are used as an impregnation substance by permeating or absorbing said agents in a substrate such as paper, cloth, and water absorbable polymers, the sublimating of said agents from the surface during drying will decrease their antimicrobial properties. Also when said impregnation substances are used, the antimicrobial agents will be volatized, dissolved and deposited from the surface of said substances and then unwanted harmful damage may occur. Accordingly, in view of stability and safety, the use and preservation of impregnation substances present difficult problems. When the organic antimicrobial agents are directly added to the films and compact resins, the antimicrobial properties may be lost by the decomposition and sublimation of the antimicrobial agents. It is difficult to process said agents without the loss of its antimicrobial properties.

Methods where inorganic and organic antimicrobial agents are absorbed in zeolite and the treatments thereof are known. However, the problem is that zeolite absorbs comparatively small amounts of the antimicrobial agent. When ceramics such as $SiO_2$, $CaCo_3$ and $Ca_3(PO_4)_3$ are used in place of zeolite, the retention of antimicrobial agent in said ceramics is relatively small. When ceramics containing antimicrobial agents are added to products such as the cosmetics, resins, fibers, papers and filters to obtain an antimicrobial property, it is necessary to use large amounts of said ceramics to have a sufficient antimicrobial properties. However, then the quality of the product is decreased since it contains large amounts of said ceramics.

SUMMARY OF THE INVENTION

The object of this invention is to provide antimicrobial hydroxyapatite powders having good affinity for a living body and a strong antimicrobial property without loss of its antimicrobial properties by sublimating, vaporizing, solubilizing and deposition of the antimicrobial agents. Further an object of this invention is to provide antimicrobial hydroxyapatite powders having stability, safety, consistent quality and capable of being used by mixing with other substances and without having to consider contamination by unwanted bacteria. Further an object of this invention is to provide methods for preparing them.

As discussed above, hydroxyapatites have good affinity for a living body and various applications. However, unwanted bacteria are easily bred on hydroxyapatites. In this invention, hydroxyapatites can be used as living body materials by providing antimicrobial properties to the hydroxyapatites, and conventional hydroxyapatites easily breeding unwanted bacteria are changed to new hydroxyapatites having good affinity for the living body, non-breading bacteria, and easy treatment. Hinokitiol, tannin, lysozyme, protamine and sorbic acid can be used as the antimicrobial agents. However, hinokitiol has a comparative vaporization property and hinokitiol and tannin are likely to be oxidized in the atmosphere. The antimicrobial properties and color of hinokitiol and tannin are changed in the presence of metals, and thus specific methods are necessary to keep said properties for long period of time with respect to hinokitiol and tannin.

Lysozyme is the basic enzyme and the treatment thereof is difficult. Protamine is water soluble and the applicable areas are limited. Sorbic acid is oxidized and colored in the atmosphere, and also when the solution is heated, the vaporization of sorbic acid occurs unexpectedly with the steam. However, when these antimicrobial agents are absorbed in hydroxyapatites the agents that are absorbed in hydroxyapatites are not solubilized and deposited into solutions treated with hydroxyapatites. Further, absorbed antimicrobial agents are stable to heat treatment and do not change in quality, and their antimicrobial properties are maintained for a long period of time.

Thus it is an the object of this invention is to provide antimicrobial hydroxyapatites wherein antimicrobial metal ions and one or more antimicrobial agents selected from hinokitiol, tannin, lysozyme, protamine and sorbic acids are absorbed in the hydroxyapatites. In certain cases, antimicrobial metal ions are substituted for the calcium ions in hydroxyapatites or said metal ions enter into the holes of the apatite crystals. It is also possible for them to coexist with antimicrobial metal phosphates. The antimicrobial metal ions used in the present invention are silver, copper and zinc ions.

The antimicrobial hydroxyapatites containing the antimicrobial metal ions are stable and heat resistant. It is possible to use the antimicrobial hydroxyapatites with living body materials, because they are in the form of powders.

DETAILED DESCRIPTION OF THE INVENTION

Hydroxyapatites used in this invention are the synthetic and natural hydroxyapatites as shown by the formula $Ca_{10}(PO_4)_6(OH)_2$. Apatites in which a part of the OH radical is changed to $F^-$ or $Br^-$ can be also used.

Antimicrobial hydroxyapatites containing antimicrobial metal ions can be produced by having antimicrobial metal salts present when the hydroxyapatites are produced or by reacting the hydroxyapatites with the antimicrobial metal salts.

For example, a calcium chloride solution can be dripped into or otherwise added to a solution containing di-sodium mono hydrogen phosphate and an antimicrobial metal salt selected from silver, copper and zinc salts. The hydroxyapatite is produced from this solution by the usual method. The hydroxyapatite produced is then filtered, washed with distilled water, dried and crushed. Or, hydroxyapatites produced first by the usual method can be suspended in water and water soluble antimicrobial metal salts added to the suspension. Then, the precipitates are washed with distilled water, dried and crushed. The acid radicals, metal salts and calcium salts produced by changing the calcium ions of hydroxyapatite to one of three metal ions, coexist with the antimicrobial hydroxyapatites. Thus it is necessary to remove these contaminating substances by washing fully the antimicrobial hydroxyapatites with water.

The amounts of antimicrobial metal ions contained in the hydroxyapatites are optionally adjusted by the kinds of antimicrobial metal salts used, the concentrations of the solutions treated and the reaction temperature. However, if the structure of the antimicrobial hydroxyapatite as produced is changed from the apatite structure, then it is preferable to limit the amounts of metal salts per hydroxyapatite to 30% or less, preferably from 0.0001 to 5%.

The antimicrobial hydroxyapatites obtained retain their antimicrobial properties for a long period of time and the amounts of metal soluble in water are ppm or less. Thus the products can be used safely and their antimicrobial properties taken advantage of by adding the hydroxyapatites in amounts of 10% or less, preferably 0.5-5% to other materials.

Antimicrobial hydroxyapatites, wherein at least one antimicrobial agent selected from hinokitiol, tannin, lysozyme, protamine and sorbic acid is contained in the hydroxyapatite can be produced by dissolving the agent in water and then adding the solution to hydroxyapatite powders. Then the powders are washed with water, so that any antimicrobial agent not absorbed by the hydroxyapatite is completely washed out. The antimicrobial hydroxyapatites are then dried and crushed. Also when hydroxyapatites are produced by usual wetting method, the antimicrobial agents coexist with the materials of hydroxyapatite.

The amounts of antimicrobial agents to be absorbed by the hydroxyapatites depend upon the type of antimicrobial agents used, the solution concentration, and the methods for using said hydroxyapatites. However, the amounts of antimicrobial agents to be absorbed are limited to 0.01-10% per hydroxyapatite.

The antimicrobial hydroxyapatites obtained in this method preserve the antimicrobial properties for a long period of time and the antimicrobial agents carried by the hydroxyapatites are not soluble in water and alcohol. Then, the hydroxyapatites can be used safely and the antimicrobial properties utilized by adding the hydroxyapatites to other materials at the rate of 50% or less, preferably 0.1-20%.

The antimicrobial hydroxyapatites of this invention are useful, because they are safe and have good affinity for a living body, in the fields of foods, living body materials, cosmetics, fibers, celluloses, plastics, filters and water absorption polymers where antimicrobial properties are needed. When used in a dentifrice, an anticaries effect is obtained by the protein removing action and by the fine filling effect of hydroxyapatite. Pharmaceutical agents stay on the surface of a tooth with hydroxyapatite for a long period of time and the highly preventive agents of dental caries are developed by this invention.

The present invention will be now described in detail with reference to the following examples.

EXAMPLE 1

8 g of copper sulfate are added and dissolved in 1.2 l of an 0.1 M solution of $Na_2HPO_4$. 1 l of 0.1 M $CaCl_2$ solution is added dropwise with stirring to said solution. Hydroxyapatites are produced by the usual method. The products are washed with the distilled water fully, dried and crushed. Antimicrobial hydroxyapatite powders containing copper are obtained.

EXAMPLE 2

The same procedure as Example 1 is preformed except that about 6 g of zinc sulfate are used in place of copper sulfate. Antimicrobial hydroxyapatite powders containing zinc are obtained.

EXAMPLE 3

The same procedure as Example 1 is performed except that copper sulfate, about 1 g, and zinc sulfate, about 2 g, are used in place of copper sulfate. Antimicrobial hydroxyapatite powders containing zinc and copper are obtained.

EXAMPLE 4

About 2 g of silver nitrate are dissolved into 1 l distilled water and the pH is adjusted to alkali from neutral by adding ammonia water and stirring. 1,000 ml of 0.1 M $CaCl_2$ solution and 600 ml of 0.1 M $Na_2HPO_4$ solution are added dropwise respectively. Hydroxyapatites are produced by adjusting from neutral to alkali with ammonia water by usual method. The products obtained are washed thoroughly with distilled water, dried and crushed. Antimicrobial hydroxyapatite powders containing silver are obtained.

EXAMPLE 5

The same procedure as Example 4 is performed except that 0.1 g of silver nitrate, 0.2 g of copper sulfate and 0.4 g of zinc sulfate are used in place of the silver nitrate. Antimicrobial hydroxyapatite powders containing silver, copper and zinc are obtained.

EXAMPLE 6

1 g of silver nitrate and 0.8 g of copper sulfate are added to 100 ml of 1 M calcium hydroxide solution and further 0.2 M phosphate solution is added with stirring. Hydroxyapatites are produced by the usual method. The products are fully washed with distilled water, dried and crushed. Antimicrobial hydroxyapatite powders containing silver and copper are obtained.

EXAMPLE 7

The same procedure as Example 6 is performed except that 2 g of zinc sulfate and 0.4 g of sodium fluoride are used in place of the silver nitrate and copper sulfate. Antimicrobial hydroxyapatite powders containing zinc and fluoride are obtained.

EXAMPLE 8

10 g of hydroxyapatite, 0.5 g of silver nitrate and 1.3 g of zinc sulfate are added to 100 ml of distilled water with stirring. The products are fully washed with the distilled water, dried and crushed. Antimicrobial hydroxyapatite powders containing silver and zinc are obtained.

EXAMPLE 9

The same procedure as Example 8 is performed except that 0.8 g of copper sulfate are used in place of the silver nitrate. Antimicrobial hydroxyapatite powders containing zinc and copper are obtained.

EXAMPLE 10

1 g of the antimicrobial hydroxyapatite powders prepared in the above examples are added to 100 ml of distilled water with stirring. Then the dissolved amounts of metals are measured. The results show that the dissolved amounts of metals are below 100 ppb.

EXAMPLE 11

Sample compositions are prepared by adding the antimicrobial hydroxyapatite powders obtained in Examples 1-9 to hydroxyapatite at the rate of 1%. The antimicrobial results of said compositions are shown respectively as follows:

| bacteria | Passing time and number of bacteria | |
|---|---|---|
| | 0 hour | after 48 hours |
| E. coli | $5.2 \times 10^4 - 4.3 \times 10^5$ | <10 |
| staphylococcus aureus | $6.1 \times 10^4 - 1.4 \times 10^5$ | <10 |
| Ps. aeruginosa | $1.5 - 8.6 \times 10^5$ | <10 |

EXAMPLE 12

The products obtained in Example 8 are added to 100 ml of a slurry comprising 100 g of hydroxyapatite and 200 ml of distilled water at a rate of 0.001%, 0.005%, 0.01% and 0.1% respectively.

| Amounts added (%) | bacteria | Passing time and number of bacteria | |
|---|---|---|---|
| | | 0 hours | after 48 hours |
| 0.001 | E. coli | $5.5 \times 10^6$ | $5.0 \times 10^6$ |
| 0.005 | E. coli | $3.6 \times 10^6$ | <10 |
| 0.01 | E. coli | $2.3 \times 10^5$ | <10 |
| 0.1 | E. coli | $7.3 \times 10^5$ | <10 |

The results show that additions of 0.005% or more are effective.

EXAMPLE 13

Binders are added to the products obtained in Example 5 and are compacted for molding. The molded products are sintered at 500° C. and pellets having a diameter of 3 cm are obtained. The pellets produced are pure antimicrobial hydroxyapatite. The antimicrobial activity test is performed by using said pellets and the following results are obtained.

| bacteria | passing time and number of bacteria | |
|---|---|---|
| | 0 hour | after 48 hours |
| E. coli | $6.8 \times 10^4$ | <10 |

It is clear from the results of Examples 11–13 that antimicrobial hydroxyapatite powders can be used from a concentration of 100% to concentrations as low as 0.005% when other materials are mixed with them.

EXAMPLE 14

1.0 kg of hydroxyapatite and 0.0016 g of silver nitrate are added to 10 l of distilled water and stirred for 1 hour with heating. The products are fully washed with distilled water, dried and crushed.

Antimicrobial hydroxyapatite powders containing 0.001% silver are obtained. The dissolving test is performed on this product and no silver is dissolved. The antimicrobial activity test is performed by using a composition comprising 1% of said product and 88% of hydroxyapatite. Hydroxyapatite is used as a control.

The results are as follows:

| bacteria | passing times and number of bacteria | | |
|---|---|---|---|
| | 0 hour | after 6 hours | after 24 hours |
| The antimicrobial hydroxyapatite / E. coli | $2.4 \times 10^7$ | $1.0 \times 10^6$ | <10 |
| Control / E. coli | $2.4 \times 10^7$ | $3.0 \times 10^8$ | $1.0 \times 10^{10}$ |

EXAMPLE 15

1.5 g of hinokitiol is dissolved in ethanol and 100 g of hydroxyapatite are added to said solution with stirring. The products are fully washed with ethanol and distilled water, dried and crushed. Antimicrobial hydroxyapatite powders containing 1.5% hinokitiol are obtained.

EXAMPLE 16

1.0 g of hinokitiol and 0.4 g of tannin are dissolved in ethanol and hydroxyapatite is added with stirring to said solution. The products are washed fully with ethanol and distilled water, then dried and crushed. Antimicrobial hydroxyapatite powders containing 1.0% hinokitiol and 0.4% tannin are obtained.

EXAMPLE 17

5 g of lysozyme are dissolved in distilled water and 100 g of hydroxyapatite are added to said solution with stirring. The products are fully washed with ethanol and distilled water, then dried and crushed. Antimicrobial hydroxyapatite powders containing 5% lysozyme are obtained.

EXAMPLE 18

2.0 g of Protamine are dissolved in 500 ml of distilled water and hydroxyapatite is added with stirring to said solution. The products are fully washed with the distilled water, dried and crushed. Antimicrobial hydroxyapatite powders containing 2% protamine are obtained.

EXAMPLE 19

2.0 g of sorbic acid are dissolved in 500 ml of ethanol and 100 g of hydroxyapatites are added with stirring. The products are fully washed with ethanol and distilled water, dried and crushed.

Antimicrobial hydroxyapatite powders containing 2% sorbic acid are obtained.

EXAMPLE 20

50 ml of a 10% hinokitiol solution are added to 1 l of 1 M $Ca(OH)_2$ solution and further 0.2 M phosphate solution is added with stirring. Hydroxyapatites are produced by the usual method. The products are fully washed with ethanol and distilled water, dried and crushed. Antimicrobial hydroxyapatite powders containing 5% hinokitiol are obtained.

EXAMPLE 21

10 g of the antimicrobial hydroxyapatite powders prepared in the above Examples ar suspended in 100 ml of distilled water and stirred. The dissolved amounts of antimicrobial agent are measured. The results show that said agents are not dissolved in any cases.

EXAMPLE 22

Antimicrobial activity tests are performed on the products obtained in Examples 15–19 and the results are as follows:

|  | bacteria | 0 hour | after 24 hours |
|---|---|---|---|
| Example 15 | E. coli | $4.1 \times 10^5$ | <10 |
| Example 16 | E. coli | $3.2 \times 10^4$ | <10 |
| Example 17 | Bacillus subtilis | $5.0 \times 10^5$ | $2.6 \times 10^3$ |
| Example 18 | Bacillus subtilis | $6.9 \times 10^6$ | $8.4 \times 10^5$ |

-continued

|  | bacteria | 0 hour | after 24 hours |
|---|---|---|---|
| Example 19 | Bacillus subtilis | $9.5 \times 10^5$ | $2.1 \times 10^4$ |

EXAMPLE 23

The products obtained in Example 20 are added to a slurry comprising 100 g of hydroxyapatite and 200 ml of distilled water at a rate of 0.2% and 1.0% respectively. Antimicrobial tests for E.coli are performed and the results are as follows:

| Amounts added | 0 hour | after 24 hours |
|---|---|---|
| 0.2% | $1.0 \times 10^{10}$ | $1.5 \times 10^8$ |
| 1.0% | $1.0 \times 10^{10}$ | <10 |
| Control | $1.0 \times 10^8$ | $2.3 \times 10^{12}$ |

The antimicrobial properties and bacteriostatic properties of the antimicrobial hydroxyapatite powders are demonstrated by the antimicrobial tests of Examples 22 and 23.

REFERENCE EXAMPLE 1

Ceramics powders (hydroxyapatite, $CaHPO_4$, $CaH_4(PO_4)_3$, $Ca_3(PO_4)_2$, hyrophosphate calcium and zeolite) are added to a hinokitiol solution of various concentrations and hinokitiols are absorbed by the ceramics with stirring. Said ceramics are fully washed with ethanol and distilled water and hinokitiol which is not absorbed is washed out of the ceramics. Then the amounts of hinokitiol absorbed by the ceramics are measured.

The results shown in Table I are the maximum amounts absorbed.

TABLE I

| Sample | max. amounts absorbed (%) |
|---|---|
| hydroxyapatite | 3.20 |
| $CaHPO_4$ | 0.04 |
| $CaH_4(PO_4)_2$ | 0.03 |
| $Ca_3(PO_4)_2$ | 0.14 |
| pyrophosphate Ca | 0.09 |
| zeolite | 0.05 |

REFERENCE EXAMPLE 2

The maximum absorbed amounts of various organic antimicrobial agents with hydroxyapatite, $Ca_3(PO_4)_2$ and zeolite are measured.

The results are shown in Table II.

TABLE II

| | maximum absorbed amounts (%) | | |
|---|---|---|---|
| antimicrobial agent | hydroxyapatite | $Ca_3(PO_4)_2$ | zeolite |
| tannin | 0.8 | <0.03 | <0.03 |
| lysozyme | 10.0 | 3.4 | 5.0 |
| protamine | 3.0 | 0.4 | 0.1 |
| sorbic acid | 3.0 | <0.03 | 0.1 |
| clove oil | <0.03 | <0.03 | <0.03 |
| glycine | <0.03 | <0.03 | <0.03 |
| betaine | <0.03 | <0.03 | <0.03 |
| clorhexidine HCl | <0.03 | <0.03 | <0.03 |

It is clear in the Reference Examples I and II that hinokitiol, tannin, lysozyme, protamine and sorbic acid are remarkably absorbed in hydroxyapatite, when compared with other ceramics.

What is claimed is:

1. An antimicrobial hydroxyapatite powder comprising hydroxyapatite powder having absorbed therein silver ions.

2. The antimicrobial hydroxyapatite powder of claim 1, wherein the powder contains from 0.0001 to 5% by weight of the silver ions.

3. The antimicrobial hydroxyapatite powder of claim 1 which also contains at least one metal ion selected from the group consisting of copper and zinc ions.

4. A method for preparing the antimicrobial hydroxyapatite powder of claim 1, comprising adding a calcium chloride solution to a solution containing disodium monohydrogen phosphate and at least one silver salt to form a precipitate of hydroxyapatite containing silver ions, collecting and washing the precipitate, and thereafter drying and crushing the precipitate to form said powder.

* * * * *